United States Patent [19]

Pachur

[11] Patent Number: 5,808,183
[45] Date of Patent: Sep. 15, 1998

[54] PROCESS FOR CALCULATING THE TRANSITION TEMPERATURE CURVE OF IRRADIATED LOW-ALLOY REACTOR PRESSURE VESSEL STEEL

[76] Inventor: Dieter Pachur, Auf der Klause 10, D-52428 Jülich, Germany

[21] Appl. No.: 765,237
[22] PCT Filed: May 30, 1995
[86] PCT No.: PCT/DE96/00736
  § 371 Date: Dec. 17, 1996
  § 102(e) Date: Dec. 17, 1996
[87] PCT Pub. No.: WO95/35499
  PCT Pub. Date: Dec. 28, 1995

[30] Foreign Application Priority Data

Jun. 20, 1994 [DE] Germany .......................... 44 21 009.4

[51] Int. Cl.⁶ .......................... G01N 17/00; G01N 25/02; G01N 33/20
[52] U.S. Cl. ..................... 73/86; 73/87; 374/53
[58] Field of Search ............................ 73/86, 87; 374/53

[56] References Cited

FOREIGN PATENT DOCUMENTS 6789 7/1989 WIPO .

OTHER PUBLICATIONS

Patent Abstracts of Japan vol. 12, No. 161, (P-702), Ab. Date May 17, 1988 (62–274258) "Method for Evaluating and Testing Characteristic to Stop Brittle Crack Propagation".
Patent Abstracts of Japan vol. 8, No. 163, (P-290) Ab Date Jul. 27, 1984 (59–60347) "Method for Evaluating Deteriotion Degree of Low-Alloy Heat-Resistant Steel".

Primary Examiner—Thomas P. Noland
Attorney, Agent, or Firm—Herbert Dubno

[57] ABSTRACT

The transition temperature curve of irradiated low-alloy reactor pressure steel is calculated utilizing results from a notched impact bending test performed on irradiated samples of steel. The transition temperature curves for the partial energy, the hydrogen and oxygen concentrations and the metallographic structure are determined and the transition temperature curve is calculated therefrom.

2 Claims, 2 Drawing Sheets

PROCESS FOR CALCULATING THE TRANSITION TEMPERATURE CURVE OF IRRADIATED LOW-ALLOY REACTOR PRESSURE VESSEL STEEL

CROSS REFERENCE TO RELATED APPLICATION

This application is a national stage of PCT/DE95/00736 filed 30 May 1995 published as WO95/35499 Dec. 28, 1995 and based upon German national application P44 21 009.4 of Jun. 20, 1994 under the International Convention

FIELD OF THE INVENTION

The invention relates to a method for calculating the transition temperature curve of irradiated low-alloy reactor pressure vessel steel for the irradiation temperature range of 250°–320° C.

BACKGROUND OF THE INVENTION

In order to evaluate the brittle fracture safety of safety-relevant components in reactor technology, knowledge of the change in mechanical properties as a function of neutron flux is required. In current practice, test specimens are irradiated in the nuclear reactor and removed and examined at defined time intervals. The condition of a component of the same material in the reactor is inferred from these results. An additional safety-related calculation of embrittlement is performed using the US-NRC rules Reg.Guide 1.99 ff and the German KTA rules based thereon. Copper and nickel contents of the steel must be known for the application of these rules.

OBJECT OF THE INVENTION

It is the object of the invention to calculate the embrittlement of a reactor pressure vessel in operation.

SUMMARY OF THE INVENTION

This object is achieved according to the invention by a procedure wherein the transition temperature curve of irradiated low-alloy reactor pressure vessel steel for the irradiation temperature range of 250° to 320° C. is calculated in that the instrumented Charpy impact test is carried out with unirradiated material specimens of the pressure vessel steel determining transition temperature curves for the partial energy values Ea, Eb and Ec. The hydrogen concentration $K_{H2}$ (specified in ppm) of the unirradiated material specimens of the steel, the oxygen concentration $K_{O2}$ (specified in ppm) of the unirradiated material specimens of the steel and their metallographic microstructure are determined. The energy decrease $\Delta Ea$ for the case of saturation irradiation is determined according to the relation $$\Delta Ea = 0.316 \cdot \alpha \cdot K_{H2}$$

and the energy decrease $\Delta Eb$ for the case of saturation irradiation is determined according to the relation $$\Delta Eb = 0.63 \cdot \beta \cdot K_{H2}.$$

The increase in transition temperature for the transition temperature curves of the partial energy values Ea, Eb and Ec for the case of saturation irradiation is determined according to the relation $$\Delta TT = (\alpha + \beta) \cdot K_{H2} + 30 + 0.244 \cdot K_{O2}.$$

The values determined for $\Delta Ea$ and $\Delta TT$ are used to determine the transition temperature curve for the partial energy Ea for the case of a material specimen irradiated up to saturation, the values determined for $\Delta Eb$ and $\Delta TT$ are used to determine the transition temperature curve for the partial energy Eb for the case of a material specimen irradiated up to saturation, and the values determined for $\Delta TT$ are used to determine the transition temperature curve for the partial energy Ec for the case of a specimen irradiated in saturation.

The transition temperature curves thus determined for the partial energies are then superimposed to determine the transition temperature curve for the pressure vessel steel for the case of saturation irradiation, with $$\alpha = 333$$

and $$\beta = 0$$

for a ferritic-perlitic microstructure of the material specimen, with $$\alpha = 0$$

and $$\beta = 166$$

for a martensitic microstructure of the material specimen and with $$\alpha = 166$$

and $$\beta = 83$$

for the bainite structure of the material specimen.

The transition temperature increase for preselected energy values can be determined by comparing the calculated transition temperature curve for the irradiated pressure vessel steel with the transition temperature curve determined by Charpy impact tests of unirradiated material specimens.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
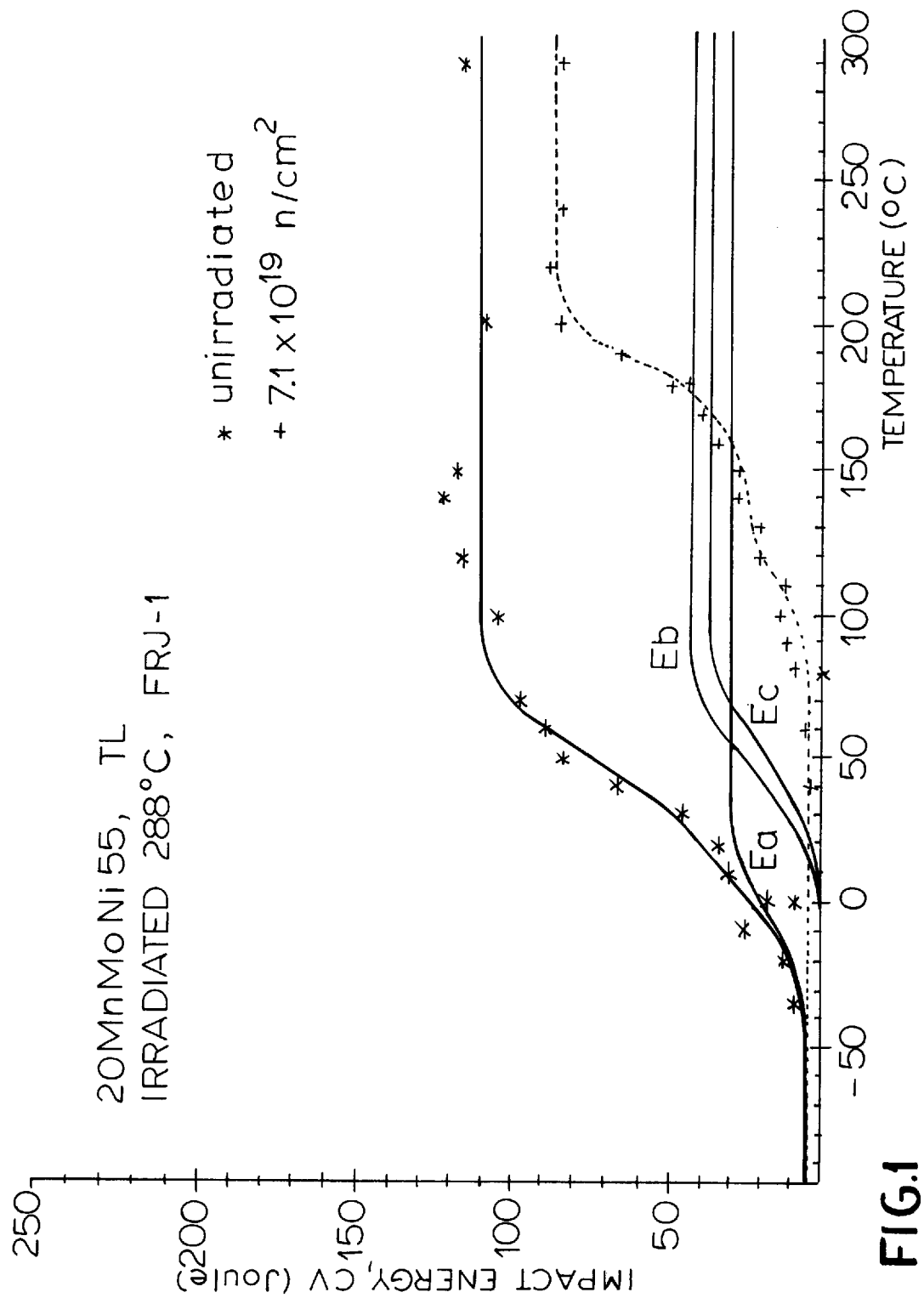
FIG. 1 is a graph of impact energy vs temperature illustrating the invention.

In the following, the method will be described by which the change in mechanical characteristics due to reactor irradiation is calculated from gas analyses and microstructural investigations of unirradiated specimens.

Calculations are performed to determine the mechanical characteristics of the instrumented Charpy impact test for irradiated specimens. These are the transition temperature values at the impact energies of 41 and 68 joule used in the design codes and the transition temperature values TTa, TTb and TTc of the partial energies determined by analysing the load-time and load-distance signals in the notched bar impact bending test (see Pachur, D., *Comparison of Drop-Weight and Instrumented Charpy Impact Test Results for Irradiated RPV, ASTM STP*1175, 1993, 195–210).

Reactor irradiation shifts all the above transition temperatures towards higher values and decreases the partial energy values.

Method:

The changes in mechanical characteristics due to reactor irradiation were found to be dependent on the hydrogen content of the chemical hydrogen compounds ($H_2$, $H_2O$, $CH_n$) in the steel specimens, on the oxygen content of the chemical oxygen compounds ($O_2$, CO, $CO_2$, MeO) in the steel specimens and on the microstructure of the steel used.

An additional parameter is the irradiation temperature. At irradiation temperatures between 50° and 150° C., a total of four defect mechanisms are formed which recover with increasing temperature (see Pachur, D., *Nuclear Technology*, Vol. 59, December 1982, 463–475). The behavior of irradiation defects in the material is described by the defect mechanisms. Defect mechanism no.1 was allocated to vacancies with a few angstrom in diameter and defect mechanism no.2 to vacancy accumulations. Existing hydrogen compounds and oxygen compounds stabilize vacancies and thus contribute to the formation of the other defect mechanisms.

Defect formation is thus dependent on the irradiation temperature. Defect mechanisms no.2, no.3 and no.4 arise in the irradiation temperature range of 250°–320° C.

Each mechanism contributes to the increase in transition temperature. The increases in transition temperature allocated to the defect mechanisms were found to rise exponentially with neutron flux.

The maximum possible value of transition temperature increase due to the two defect mechanisms no.2 and no.3 is determined by hydrogen measurement of a specimen using the relation between transition temperature increase and hydrogen content measured for irradiated specimens. Since the metallographic microstructure was found to be decisive for the allocation of the hydrogen amount to defect mechanisms no.2 and no.3, the contributions of defect mechanisms no.2 and no.3 can be separated when the microstructure is known.

The maximum possible value of transition temperature increase due to defect mechanism no.4 is determined from the oxygen measurement of a specimen using the relation between transition temperature increase and oxygen content measured for irradiated specimens.

The total increase in transition temperature is formed by the sum of the transition temperature increases belonging to the different defect mechanisms. The exponential factors of the individual components determined experimentally by irradiation tests are used to calculate the increase with neutron fluence.

The transition temperature increases due to defect mechanisms no.2 and no.3 obtained are additionally used to determine the decrease of the energy fractions $\Delta Ea$ and $\Delta Eb$ belonging to these defect mechanisms using the relation between $\Delta E$ and $\Delta TT$ ascertained in irradiation experiments.

The decrease in total energy is the sum of the decreases of the energy fractions. The respective exponential factors used for calculating the transition temperature increase are used to calculate the decrease with increasing neutron fluence.

Advantages of the Method:

The embrittlement of a low-alloy steel due to reactor irradiation, expressed by transition temperature increase and upper shelf energy decrease, is calculated from the condition of unirradiated specimens. In comparison to previous purely empirical-statistical calculations of the transition temperature increase at 41 joule (US Reg.Guide, KTG rules), the method described is based on explored defect mechanisms and their behaviour during reactor irradiation. This naturally leads to a signficantly lower risk in predicting radiation embrittlement.

The recovery of the radiation damage of an embrittled reactor pressure vessel by heat treatment can be achieved selectively and with predictable success using now existing knowledge about the contributions of the different temperature-dependent defect mechanisms.

The method also permits a definition of the manufacturing conditions leading to less radiation-sensitive reactor construction steels. Suitable heat treatment can influence both the steel microstructure and the amount of dissolved gases.

EXAMPLE

The method is illustrated by the values of a MnMoNi steel. This steel exhibits bainite. A hydrogen content of 0.4 ppm and an oxygen content of 40 ppm were measured.

The transition temperature curve measured in the unirradiated state is shown in FIG. 1. This diagram also contains the energy fractions Ea, Eb and Ec taken from the load-distance diagrams of the instrumented Charpy impact test.

The example relates to a reactor irradiation at 288° C. during which defect mechanisms no.2, no.3 and no.4 can be formed.

Depending on the metallographic microstructure, the hydrogen content is apportioned to the two defect mechanisms no.2 and no.3. In the case of a ferritic-perlitic microstructure only defect mechanism no.2 is formed, in the case of a martensitic mcirostructure only defect mechanism no.3 and in the case of bainite defect mechanism no.2 as well as no.3.

The following relations were experimentally determined for the different microstructures:

The transition temperature increase for a ferritic-perlitic microstructure due to the formation of defect mechanism no.2 is $\Delta TT2_{max}=333 \cdot K_{H2}$ (Celsius) and the associated decrease in partial energy is $\Delta Ea_{max}=0.316 \cdot \Delta TT2_{max}$.

The transition temperature increase for a martensitic microstructure due to the formation of defect mechanism no.3 is $\Delta TT3_{max}=166 \cdot K_{H2}$ (Celsius) and the associated decrease in partial energy is $\Delta Eb_{max}=0.63 \cdot \Delta TT3_{max}$ (joule).

The transition temperature increase for bainite microstructures due to the formation of defect mechanisms no.2 and no.3 is $\Delta TT_{max}$ (bainite)=$250 \cdot K_{H2}$ (Celsius). The following contributions result for bainite taking into consideration the relation between transition temperature increase and hydrogen content for ferritic-perlitic microstructures (defect mechanism no.2) and for martensitic microstructures (defect mechanism no.3):

$$\Delta TT2_{max}=166 \cdot K_{H2} \text{ (Celsius)}$$

$$\Delta TT3_{max}=83 \cdot K_{H2} \text{ [Celsius]}.$$

The associated partial energy decreases are $$\Delta Ea_{max}=52.4 \cdot K_{H2} \text{ (joule)}$$

$$\Delta Eb_{max}=52.4 \cdot K_{H2} \text{ [joule]}.$$

The hydrogen concentration $K_{H2}$ is always specified in ppm.

For a hydrogen value of 0.4 ppm, $$\Delta TT2_{max}=66° \text{ C.}$$

and $\Delta TT3_{max}=33°$ C., $\Delta Ea_{max}=20$ joule and $\Delta Eb_{max}=20$ joule.

The following relation was experimentally determined for the relation between transition temperature increase due to the formation of defect mechanism no.4 and oxygen content:

$\Delta TT4_{max}=30+0.244 \cdot K_{O2}$ (Celsius), the oxygen concentration being specified in ppm.

For an oxygen value of 40 ppm $\Delta TT4_{max}=40°$ C.

The total maximum transition temperature increase at 288° C. irradiation temperature is thus $\Delta TT_{max}=\Delta TT2_{max}+\Delta TT3_{max}+\Delta TT4_{max}=140°$ C.

The increase in transition temperature with neutron fluence is then obtained by using the exponential factors $k=5 \cdot 10^{-20}$ cm$^2$ and $m=3 \cdot 10^{-20}$ cm$^2$ as $\Delta TT=(\Delta TT2_{max}+\Delta TT3_{max}) \cdot (1-\exp(-k\phi t))+\Delta TT4_{max} \cdot (1-\exp(-m\phi t))$.

At a neutron fluence of $\phi t=7.1 \cdot 10^{19}$ n/cm$^2$ a transition temperature increase of 130° C. is calculated for this steel.

Using the exponential factor of transition temperature increases $\Delta TT2$, $\Delta TT3$, the following is obtained for the upper shelf energy decrease ($\Delta USE$) due to irradiation:

$\Delta USE=(\Delta Ea_{max}+\Delta Eb_{max}) \cdot (1-\exp(-k\phi t))$.

A decrease by 30 joule is thus obtained for a neutron fluence of $7.1 \cdot 10^{19}$ n/cm$^2$.

The increase of transition temperature was recorded at 50% of the maximum partial energy.

The values of transition temperature increase and upper shelf energy decrease thus determined are sufficient for a safety-related analysis of the irradiated material. Furthermore, the transition temperature curve for the irradiated material can be calculated using the method described in Pachur, D., *Comparison of Drop-Weight and Instrumented Charpy Impact Test Results for Irradiated RPV*, ASTM STP1175, 1993, 195–210 and the values now known for the transition temperature increase of the partial energies Ea, Eb and Ec and the values of the decrease of the partial energies $\Delta Ea$ and $\Delta Eb$.

Instrumented Charpy Impact Test

Figure 2:
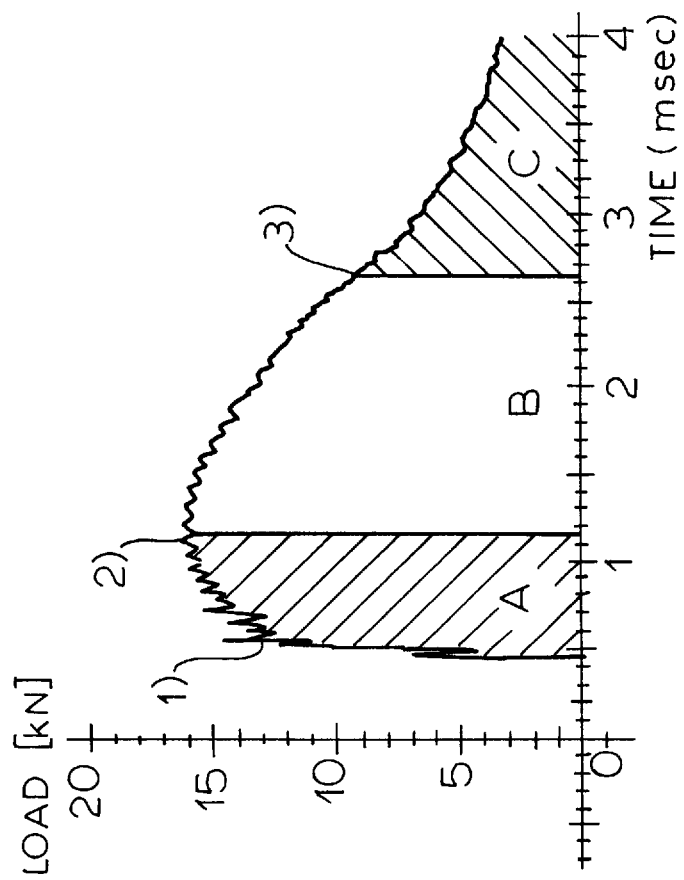
FIG. 2 is a graph of load vs time.

FIG. 2 shows the load signal of a specimen measured in the ductile fracture region. The characteristic points are *1) yield point, 2) maximum load and 3) inflection point.

*1), 2) and 3) are Part Nos.

In the Charpy impact test, the energy is measured which is necessary to cause fracture of a standard CV specimen. The non-instrumented Charpy impact test is carried out according to DIN standard 50115.

For the instrumented Charpy impact test, the German Iron and Steel Institute (Verein Deutscher Eisenhuettenleute—VDEh) has drawn up a recommendation (steel test specification SEP 1315, May 1987). The impact energy is measured by a load-time or load-distance signal. Essential parameters of the load signal are the yield point ($F_{gy}$), the maximum load ($F_m$) and the load inflection point after exceeding the maximum load. In our experiments, the energy fractions up to maximum load (Ea), from maximum load to the inflection point (Eb), and from the inflection point to the end of the load signal (Ec) are calculated from the load signals.

I claim:

1. A method for calculating the transition temperature curve of irradiated low-alloy reactor pressure vessel steel for the irradiation temperature range of 250° to 320° C., comprising the steps of:

carrying out an instrumented Charpy impact test with unirradiated material specimens of the pressure vessel steel determining transition temperature curves for the partial energy values Ea, Eb and Ec;

determining a hydrogen concentration $K_{H2}$ in ppm of the unirradiated material specimens of the steel, an oxygen concentration $K_{O2}$ in ppm of unirradiated material specimens of the steel and metallographic microstructures of the specimens;

determining an energy decrease $\Delta Ea$ for the case of saturation irradiation according to the relation $\Delta Ea=0.316 \cdot \alpha \cdot K_{H2}$ and an energy decrease $\Delta Eb$ for saturation irradiation according to the relation $\Delta Eb=0.63 \cdot \beta \cdot K_{H2}$;

determining an increase in transition temperature for transition temperature curves of partial energy values Ea, Eb and Ec for the case of saturation irradiation according to the relation $\Delta TT=(\alpha+\beta) \cdot K_{H2}+30+0.244 \cdot K_{O2}$ and using values determined for $\Delta Ea$ and $\Delta TT$ to determine the transition temperature curve for the partial energy Ea for the case of a material specimen irradiated up to saturation, and using values determined for $\Delta Eb$ and $\Delta TT$ to determine the transition temperature curve for the partial energy Eb for the case of a material specimen irradiated up to saturation, using values determined for $\Delta TT$ to determine the transition temperature curve for the partial energy Ec for the case of a specimen irradiated in saturation and superimposing the transition temperature curves thus determined for the partial energies to determine the transition temperature curve for the pressure vessel steel for the case of saturation irradiation, where $\alpha=333$ and $\beta=0$ for a ferritic-perlitic microstructure of the material specimen, $\alpha=0$ and $\beta=166$ for a martensitic microstructure of the material specimen and $\alpha=166$ and $\beta=83$ for a bainite structure of the material specimen.

2. The method defined in claim 1 wherein the transition temperature increase for preselected energy values is determined by comparing the calculated transition temperature curve for the irradiated pressure vessel steel with the transition temperature curve determined by Charpy impact tests of unirradiated material specimens.

* * * * *